US006991906B1

(12) United States Patent
Fuhr et al.

(10) Patent No.: US 6,991,906 B1
(45) Date of Patent: Jan. 31, 2006

(54) METHOD AND DEVICE FOR MEASURING, CALIBRATING AND USING LASER TWEEZERS

(75) Inventors: Günter Fuhr, Berlin (DE); Thomas Schnelle, Berlin (DE); Torsten Müller, Berlin (DE); Hermine Hitzler, Berlin (DE); Karl-Otto Greulich, Heidelberg (DE); Shamoi Monajembashi, Heidelberg (DE)

(73) Assignee: Evotec Biosystems AG, Hamburg (DE)

( * ) Notice: Subject to any disclaimer, the term of this patent is extended or adjusted under 35 U.S.C. 154(b) by 0 days.

(21) Appl. No.: 09/582,609

(22) PCT Filed: Dec. 21, 1998

(86) PCT No.: PCT/EP98/08370

§ 371 (c)(1), (2), (4) Date: Sep. 6, 2000

(87) PCT Pub. No.: WO99/34653

PCT Pub. Date: Jul. 8, 1999

(30) Foreign Application Priority Data

Dec. 28, 1997 (DE) ........................................ 197 57 785

(51) Int. Cl.
*G01N 33/53* (2006.01)
*G01N 33/543* (2006.01)

(52) U.S. Cl. ................................ 435/7.1; 435/4; 435/6; 435/7.9; 435/7.92; 435/287.1; 435/287.3; 435/288.1; 436/164; 436/172; 436/518; 436/524; 436/528; 422/50; 422/68.1; 422/81.01; 422/82.05; 422/82.13; 422/98; 204/155; 204/157.5; 204/164; 204/400; 204/403.13; 356/123; 356/337; 356/614; 356/622

(58) Field of Classification Search ..................... 435/4, 435/6, 7.1, 7.9, 7.92, 287.1, 287.3, 288.1; 436/528, 164, 172, 518, 524; 422/50, 68.1, 422/82.01, 82.05, 82.13, 98; 204/155, 157.5, 164, 400, 403.13; 356/123, 337, 614, 622, 927

See application file for complete search history.

(56) References Cited

U.S. PATENT DOCUMENTS 5,198,369 A * 3/1993 Itoh et al. ................... 356/337
5,620,857 A * 4/1997 Weetall et al. .............. 356/364

FOREIGN PATENT DOCUMENTS

EP 0564273 6/1993

OTHER PUBLICATIONS

Berichte der Bunsen–Gesellschaft für physikalische Chemie, vol. 93, No. 3, 1998 "Laser in Life Sciences".

G. Weber et al. in "Int. Rev. Cytol" vol. 131, 1992, p. 1.

(Continued)

*Primary Examiner*—Chris Chin
*Assistant Examiner*—Kartic Padmanabhan
(74) *Attorney, Agent, or Firm*—Baker Botts LLP

(57) ABSTRACT

To measure or exert optically-induced forces on at least one particle in the focus of an optical cage, the following steps are taken:

a) the focus is positioned in a microelectrode arrangement with a three-dimensional electrical field that has a field gradient which forms an electrical capture area, and the focus is at a distance from the capture are and b) the amplitude of the electrical field, the light power of the light beam forming the optical cage, and/or the distance of the capture area from the focus are varied to detect which varied field property moves the particle from the focus to the capture area or vice versa, or at least to temporarily move the particle into the capture area.

16 Claims, 9 Drawing Sheets

OTHER PUBLICATIONS

S.M. Block in "Noninvasive Techniques in Cell Biology", Wiley–Liss. New York, 1990, p. 375.
A. Ashkin in "Phys. Rev. Lett.", vol. 24, 1970, p. 156.
S.M. Block et al. in "Nature" 1990, p. 348.
L. G. Tilney et al. in "J. Cell Biol." vol. 11, 1990, p. 485.
W. Paul et al., in "Phys. Blätter", vol. 46, 1990, p. 227.
Schnelle et al. in "Biochim. Biophys. Acta", 1157, 1993, p. 127.
G. Fuhr et al. in "Biochim. Biophys. Acta", 1201, 1994, p. 353.
G. Fuhr et al. in "Topics in Current Chemistry", vol. 194, 1998, p. 84.
K. Svoboda et al. in "Ann. Rev. Biophys. Biomol. Struc.", 1994, p. 247.
D.C. Prieve et al. in "Faraday Discuss Chem. Soc.", vol. 90, 1990, p. 209.
D.C. Prieve et al. in "Applied Optics", 1993, p. 1629.
A. Ashkin in "Bio. Phys. J.", vol. 61, 1992, p. 569.
G. Fuhr et al. in "Applied Physics A", vol. 67, 1998, p. 385.
L.P. Ghislain et al. in "Rev. Sci. Instrum.", vol. 65, 1994, p. 2762.
M. Nishioka et al. in "Journal of Electrostatics", vol. 35, 1995, p. 83.
R.M. Simmons et al. in "Biophysical Journal", vol. 70, 1996, p. 1813.
K. Morishima et al. in "Proc. Of IEEE", 1997, p. 155.

* cited by examiner

METHOD AND DEVICE FOR MEASURING, CALIBRATING AND USING LASER TWEEZERS

This application is a 371 of PCT/EP98/08370 filed on Dec. 21, 1998.

The invention concerns processes and devices to measure and calibrate optical fields traps, determine optically-induced force in all three dimensions that are exerted on micrometer-sized particles, and to use optical field traps.

BACKGROUND OF THE INVENTION

Optical field traps, also called "optical tweezers", "laser tweezers" or "optical traps" have been used for approximately two decades in the fields of biotechnology, medicine and molecular biology as well and other technical fields to position and manipulate micrometer-sized and submicrometer-sized particles (G. Weber et al. in *Int. Rev. Cytol.*, Vol. 131, 1992, p. 1; S. M. Block in *Noninvasive Techniques in Cell Biology*, Wiley-Liss., New York 1990, p. 375). A. Ashkin has primarily started the development of laser tweezers (A. Ashkin in *Phys. Rev. Lett.*, Vol. 24, 1970, p. 156). The principal of capturing particles by optically-induced forces is based on the fact that, in addition to radiation pressure that continuously pushes particles away from the light source, gradient forces arise which cause particles to move into a focus or be firmly held in it or move with it. Absorption and reflection of the particles must be low while the difference of the refractive index relative to the environmental solution should be as large as possible.

In recent years, laser tweezers have primarily gained acceptance because particles that are larger than the wavelength (Mie particles) as well as particles that are smaller than the wavelength (Rayleigh particles) can be trapped when the light beam is even and highly focussed. This includes biological objects such as cells, or organelles and other cell components as well as large molecules (such as DNA) and artificial microparticles (S. M. Block et al. in *Nature,* 1990, p. 348; E. M. Bonder et al. in *J. Cell Biol.*, Vol. 11, 1990, p. 421).

W. Paul discovered electromagnetic field cages (W. Paul et al. in *Forschungsberichte des Wirtschaftsministeriums Nordrhein-Westfalen*, No. 415 and 450; W. Paul in *Phys. Blätter, Vol.* 46, 1990, p. 227). They are primarily used in elementary particle physics to trap and measure atomic particles under low gas pressures. In 1993, liquid-filled, three-dimensional microfield cages were presented for the first time using dielectrophoretic forces (T. Schnelle et al. in *Biochim. Biophys. Acta*, Vol. 1157, 1993, p. 127). If the conductivity of a suspension solution is higher than that of the average conductivity of the particle, the surface charges on the particle induced in the E field are arranged and polarized to make effective the forces acting on the particle (G. Fuhr et al. in *Biochim. Biophys. Acta*, Vol. 1201, 1994, p. 353). This principle can also be used to trap, position and move particles (T. Schnelle et al. in *Biochim. Biophys. Acta*, Vol. 1157, 1993, p. 127). Objects corresponding to the Mie and Rayleigh particles can also be held in these dielectric field cages. There have been numerous suggestions for combining both principles to increase the trapping force since the optical and electrical force fields scarcely interfere with each other (G. Fuhr et al. in *Topics in Current Chemistry*, Vol. 194, 1998, p. 84).

SUMMARY OF THE INVENTION

A previously unsolved problem is how to measure the actual optically-induced force in the optical field (laser trap) acting on a particle. There are several extremely time-consuming methods to do this requiring much equipment that can be summarized as follows:

Method I (K. Svoboda et al. in *Ann. Rev. Biophys. Biomol. Struc.,* 1994, p. 247):

A calibrated flow acts on a particle trapped in the focus of a laser. The flow speed is sought at which or just before the particles are torn from the laser focus. A capture force can be calculated from this flow speed using Stokes' law. A disadvantage of this procedure is that it is difficult to repeat measurements using the same particle, and very complicated channel structures are required to make measurements in different spatial directions. A three-dimensional measurement of force (x, y, z) is not possible. This procedure is also limited to certain particle shapes (spheres, ellipsoids) with smooth surfaces.

Method II (C. P. Dennis in *Faraday Discuss. Chem. Soc.*, Vol. 90, 1990, p. 209):

The average deflection of a particle in the laser focus is measured based on Brownian collisions. In principle, all three dimensions can be measured; however, the particle motion must be measured very precisely with submicrometer precision which cannot be done for most Mie particles since they are too large for any notable deflection. In addition, the measurements become increasingly difficult and imprecise as laser power increases, and one can only work within a very narrow laser focal range.

Method III (C. P. Dennis et al. in *Applied Optics*, 1993 p. 1629):

The investigation concerns an attempt to tear away a particle that is affixed to a substrate in a specific manner using a laser tweeter. The scattering of an evanescent surface wave with total reflection is used to determine the motion of the object in the z direction (perpendicular to the surface) with a precision in the nm range. This procedure also cannot be used in all three dimensions, and it is slow and requires a large amount of calibration and equipment. In addition, the optical radiation field close to the surface does not correspond to conditions in a free solution.

In general, there is no fast and easy-to-the use method to measure force that can be carried out in the later-to-be-used particle's environmental medium with the particle itself under the same conditions.

Another previously unsolved problem in handling microscopic particles is the measurement of intermolecular attractive forces (adhesion forces) that act between the particles. Both synthetic and natural particles based on biological materials (in particular, biological cells or cell components) tend to adhere to each other when they contact. Depending on the type of adhesion, adhesion phenomena can be divided into non-specific and specific adhesion or, depending on the type of bonds in the adhesion, it can be divided into adhesion with chemical bonds or adhesion with van der Waals bonds. Measuring the specificity, the bond type and hence the bond force of adhesion is between microscopic particles is of great interest to the fields of biology, medicine and pharmacology. There is therefore a need for quantifiable, repeatable, and non-destructive procedures to measure adhesion phenomena of individual particles, e.g. to measure the specific bonds of macromolecules (which also includes microscopic particles in this context) to biological cells to investigate the immune response or to recognize infection or other cellular diseases. Another example is the interaction between microscopic particles where specific receptor-ligand systems are active on the particle surface.

There does not exist any procedure for setting specific adhesion phenomena between individual suspended microscopic particles, or for determining the occurring bond forces.

The article by K. Morishima et al. in *Proc. Of IEEE*, 1997, p. 155, discloses the combined use of optically-induced forces and electrical field forces to manipulate bacteria. In a microscopically-observed microsystem of a cluster of bacteria, a specific bacteria is trapped and fixed with a laser tweeter while the other bacteria are moved away from the individual, fixed bacteria under the effect of the electrical field. This procedure described by K. Morishima et al. is limited in its application to the described separation of individual particles from a group of many particles. The process solely concerns turning electrical fields on or off to separate particles. An investigation of the interaction between particles is not possible. In addition, individual particles cannot be moved to an existing group particles or an aggregate of particles to attain specific interactions.

The invention is based on the object of presenting improved procedures to handle particles with laser tweezers that can in particular be used to measure optically-induced forces or bonding forces, and to exert a specific force. In particular, a process according to the invention is to be capable to measure forces faster with better reproducibility and precision. The forces that act on microscopic particles are to be measured via an electric signal in quickly repeatable and is automated manner, wherein the force is to be measured with a precision in the pN range and below in any dimensional direction. Another object of the invention is to provide devices for implementing the procedure.

In particular, the invention provides capturing at least one microscopic particle in the focus of an optical cage in a microelectrode arrangement and positioning it in reference to an electrical capture area (or capture point) that is formed by electrical field gradients in the microelectrode arrangement. The focus of the optical cage with the particle is initially positioned at a distance from the capture area, i.e., at a distance from the minimum electrical field level of the capture area that represents an electrical field cage. Then the field forces in the optical cage and/or in the electrical capture area and/or the distance between the optical cage and electrical capture area are varied until the particle moves from the focus to the capture area or vice versa. Depending on the application, the given field properties when the particle starts to move are used to measure forces according to the invention, or the transitional movement itself is used to exert specific forces.

In the procedure according to the invention, forces are generated that act on a particle or particles whose fields possess a minimum level in a microelectrode arrangement with a three-dimensional electrical field that contains electrical field gradients forming the capture area. The minimum level of the electrical field forces corresponds to the capture area. The minimum level of optically-induced forces is the focus of the optical cage. Between both minimum levels is a field barrier that depends on the amplitude of the effective electrical fields, the light power of the optical cage, and the distance between the minimum levels. Depending on the setting of these quantities, the particle or particles can be positioned within the microelectrode arrangement in a predetermined manner or (if there are numerous particles) be separated from each other.

According to one important aspect of the invention, the optically-induced forces acting on a particle in the focus of an optical cage are measured. In this embodiment, only one particle is in the focus or temporarily in the capture area of the microelectrode arrangement. The field properties, i.e., the amplitude of the electrical field, the light power and/or the distance between the minimum levels is varied until the particle moves between the minimum levels, i.e., between the focus and the capture area or vice versa. It was surprisingly determined that the transitional movement can be determined very precisely in a reproducible manner. The optically-induced forces in the optical cage can be measured from the amplitude of the electrical fields in the microelectrode arrangement required to trigger the transitional movement.

According to a second important aspect of the invention, the bonding forces between several particles (e.g. to particles) are measured. In this embodiment, one particle is in the focus of the optical cage, and one particle is in the electrical capture area. The properties of the fields in the microelectrode arrangement can be varied to determine those field properties that make the particle in the focus move toward the particle in the capture area or vice versa. This principle can be correspondingly realized with groups of particles in the focus or the capture area.

The adhesive bonding force that acts between the particles can be measured from the electrical field force and (when the measurement of bonding force is combined with the measurement of optically-induced force according to the first embodiment) the optically-induced force by observing the transitional movement or tearing-away movement between the particles. A particular advantage of the invention is that the processes can be observed and evaluated in reference to specific materials, particles, and bonding types.

According to a third important aspect of the invention, microscopic particles in a microelectrode arrangement with the cited (at least) two minimum field levels with relative, set field force can be at least temporarily positioned or joined into groups or aggregates, or the groups or aggregates can be divided into parts. The manipulation of the aggregates according to the invention is preferably combined with the above-cited aspects of the invention; it can also be used independently within predetermined (if unknown) electrical and/or optical field strengths.

The subject to the invention is also a microsystem that is adapted to create an optoelectric double cage that is generated by the simultaneous creation of at least two minimum field levels of an electrical capture area and an optical cage. A fluid microsystem possesses a microelectrode arrangement to generate the electrical capture area and a transparent structure for creating the optical cage within the microelectrode arrangement. The microsystem is preferably a fluid microsystem that can be open on one side facing the light source to generate the optical cage.

It is to be noted that the techniques used to according to the invention for creating the microsystem, generating the electrical field strengths, and generating the optical cage are known as such so that details will not be discussed in the following description.

In the following, general explanations of basic principles of the invention will first be provided.

In the laser trapping process, a particle can be held in a local equilibrium that is formed by an optical trap or an optical cage in the focus of at least one laser beam. In a high-frequency microfield cage, a particle can be held in a local equilibrium that is formed by an electrical capture area of the respective field distribution. The capture area can be formed by a point, a line, or an area depending upon the field distribution. In the following description, in a non-restrictive manner the capture area will be referred to as a point; the invention can, however be correspondingly implemented using any shape of capture area. According to the above-cited first aspect, the invention is especially based on measuring the optically-induced forces in the optical trap (optical cage) consisting of the electrical force exerted on the particle when it changes between the states of equilibrium, i.e., from the focus to the capture point or vice versa The object is hence especially solved by means of laser trapping in an electrical high-frequency micro fieldcage whose field strength and electrical field distribution are known, and that is adapted to inject the laser light required to form the optical cage. By shifting the particle trapped in the laser trap (focus) from the capture point of the field cage at low electrical trap power into a specific position at a distance from the capture point, the threshold can be precisely determined at which the electrical field returns the particle from the optical focus to the capture point or vice versa by subsequently increasing the amplitude of the electrical control signals of the field cage.

The laser light required to form the optical cage is injected by means of various design features of the microfield cage. Among these are in particular attaching at least one partial group of electrodes of the microfield cage to a substrate that is transparent and thin enough for a laser light source to be brought close enough to the microfield cage so that the focus forms in it. In practical designs of the laser tweezers, the laser light source comprises an coupling lens with a very high numerical aperture. The focal length is normally in the range of a few hundred micrometers. The preferred thickness of the transparent substrate is therefore less than the focal length of the laser light source.

Depending on the application, the invention allows measurement of qualitative and/or quantitative parameters of the optically-induced forces exerted on a particle. The optically induced forces can be quantitatively measured from just a few quantities that e.g. comprise the location of the focus and the capture point, the field distribution between the electrodes, the electrical properties of the particle and its environmental solution as well as the shape, phase angle, frequency and amplitude of all the electrode signals. All of these quantities can be deter-mined independent of the actual measurement, or beforehand using purely electrical means, or by means of a single numeric simulation of the field distribution in the high-frequency cage. The optically-induced forces that act on the particle can be measured from the amplitude of the electrical control signals of the electrical field cage when the particle changes equilibrium (transitional movement). By systematically moving a particle whose passive electrical properties are known in the x and/or y and/or z direction, the forces from the focussed laser beam that act on a particle of this size can be quantitatively determined with a high resolution.

An advantage of the invention is that the force gradient of the optically-induced forces is relatively steep so that the cited transition between equilibriums is sudden and hence easy to precisely determine.

According to the invention, this procedure can be automated and used to calibrate the laser beam. The measurements can be repeated as often as desired, executed in a few seconds, and can also use the same particle in the environment in which it will later be used. In addition to absolute values of the optically-induced forces, relative values can also be measured such as symmetrical deviations of the optical beam and its intensity profiles both close and in the focal range.

The above explanations on determining optically-induced forces are correspondingly applicable for determining bond strength since this can be described as an additional contribution to the electrical field force in the electrical capture area.

The invention can be used with any type of particle such as synthetic or biological cells or their components. The particle size can include the entire range of sizes that can be manipulated with laser tweezers, but preferably less than 200 $\mu$m.

DESCRIPTION OF THE DRAWINGS

Preferred exemplary embodiments of the invention will be further discussed in the following with reference to the accompanying drawings. The drawings show in.

DETAILED DESCRIPTION OF THE INVENTION

The invention will be described in the following referring to the combination of an octopole field cage to form the capture area and an individual capture laser to form the optical cage. The invention can however be realized with any field cage shape or several laser beams.

Figure 1:
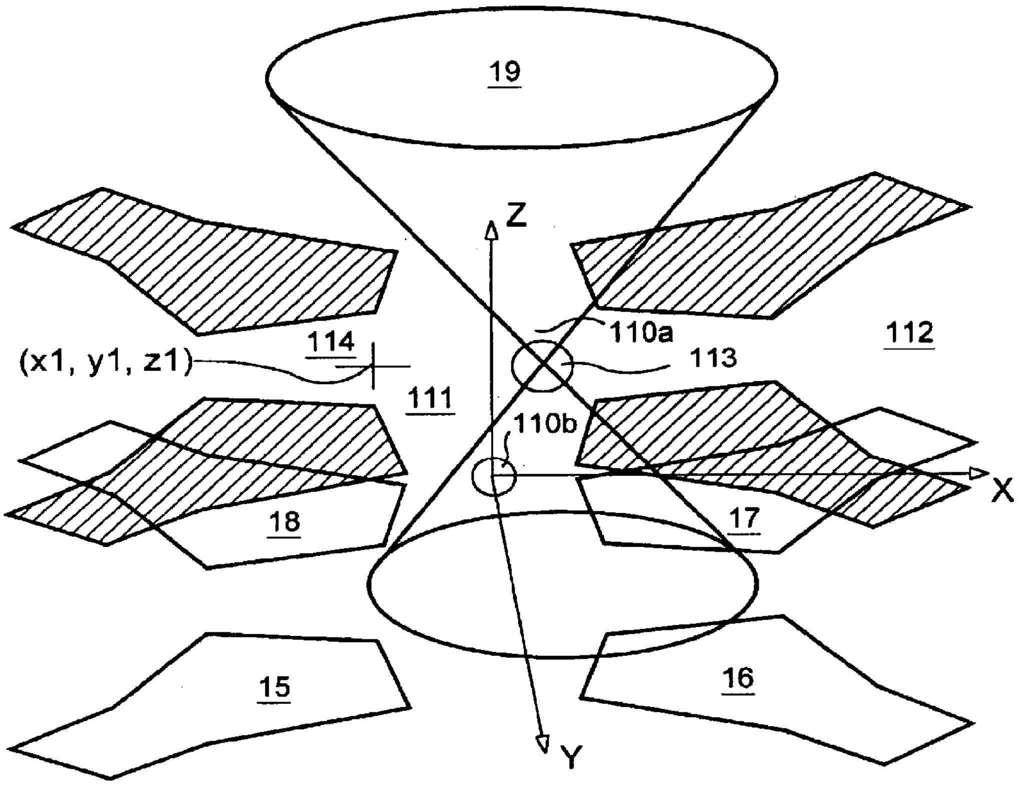
FIG. 1: a schematic representation of the arrangement of field cage electrodes and an optical cage according to a first embodiment of the invention.

FIG. 1 schematically illustrates an enlarged section of a microsystem according to the invention. The diagram only shows a microelectrode arrangement consisting of the microelectrodes 11–18 (without control lines) and a microscopic particle 113 between the microelectrodes in a suspension liquid. The microelectrodes are flat on opposing walls of the microsystem structure, and e.g. the x-y plane coincides with a substrate plane. The microelectrodes 11–18 are set up to be supplied with electrical potentials to form field gradients with one minimum field level. The technology of the electrode control to generate a specific minimum level is known per se and will therefore not be described in detail. The position of the minimum field level depends on the phases and amplitudes of the control potential at microelectrodes 11–18 and can be adjusted in a predetermined manner. The capture area or the electrical field cage is also termed a high-frequency cage since the microelectrodes are preferably supplied with high-frequency control potentials (see below for the frequency range) to manipulate the microscopic particles based on negative dielectrophoresis.

In FIG. 1, the electrical high-frequency field cage created by the microelectrodes 11–18 is combined with the focussed light beam 19 so that the focus 110*a* is in the electrical field of the microelectrodes, i.e., either in the field cage area 111 or directly adjacent 112 to the cage, while the minimum field level of the capture point 110*b* of the high frequency field cage is located at a distance (e.g. a fraction up to several particle diameters at position 114, identified by coordinates x1, y1, Z1).

The optically-induced field strengths acting on the particle 113 are measured according to the invention by first capturing the particle 113 in the focus of the laser beam and moving it by shifting the focus into the designated position (e.g. 114). The focus is shifted by mechanically changing the relative position of the microsystem and the source of the laser beam 19 by shifting devices and/or deflection devices for the laser beam which are known as such. By increasing the amplitude of the high-frequency signals applied to the electrodes, the electrical polarization force of the field cage is increased until the particle 113 is torn from the laser focus and moved into the capture point 110*b* (transitional movement between the local equilibriums in the minimum field levels).

The particle can alternately be moved between the local equilibriums by increasing the laser power and moving the particle from the capture area of the field cage into the focus and/or by moving the locations of the capture point or focus to determine the path or distance of the minimum field level at which the transitional movement occurs. Since the electrical polarization forces acting on the particle and the field distribution between the electrodes 11–18 are known, a direct proportionality exists between the measurable laser power in the focal range, the amplitude of the electrical signals, and the optically-induced forces acting on the particle. By repeating the procedure and moving the particle 113 in any spatial direction, the optically-induced forces acting on the concrete particle can be quantitatively determined. This represents an electrical calibration of the optically-induced counter-forces that is easy to set up, and it allows forces in the range of fN up to a few hundred pN to be measured.

The optically-induced forces are hence determined in at least one case from the field or location properties of the particle 113 when it moves. The electrical polarization forces acting on the particle 113 are calculated from the readily calculable field distribution between the microelectrodes 11–18 and the given locations of the focus 110*a* and capture point 110*b* when the particle is moved. These locations can be measured with a viewing microscope. In all other instances, the optically-induced forces can be relatively measured based on the cited proportionality.

Figure 2:
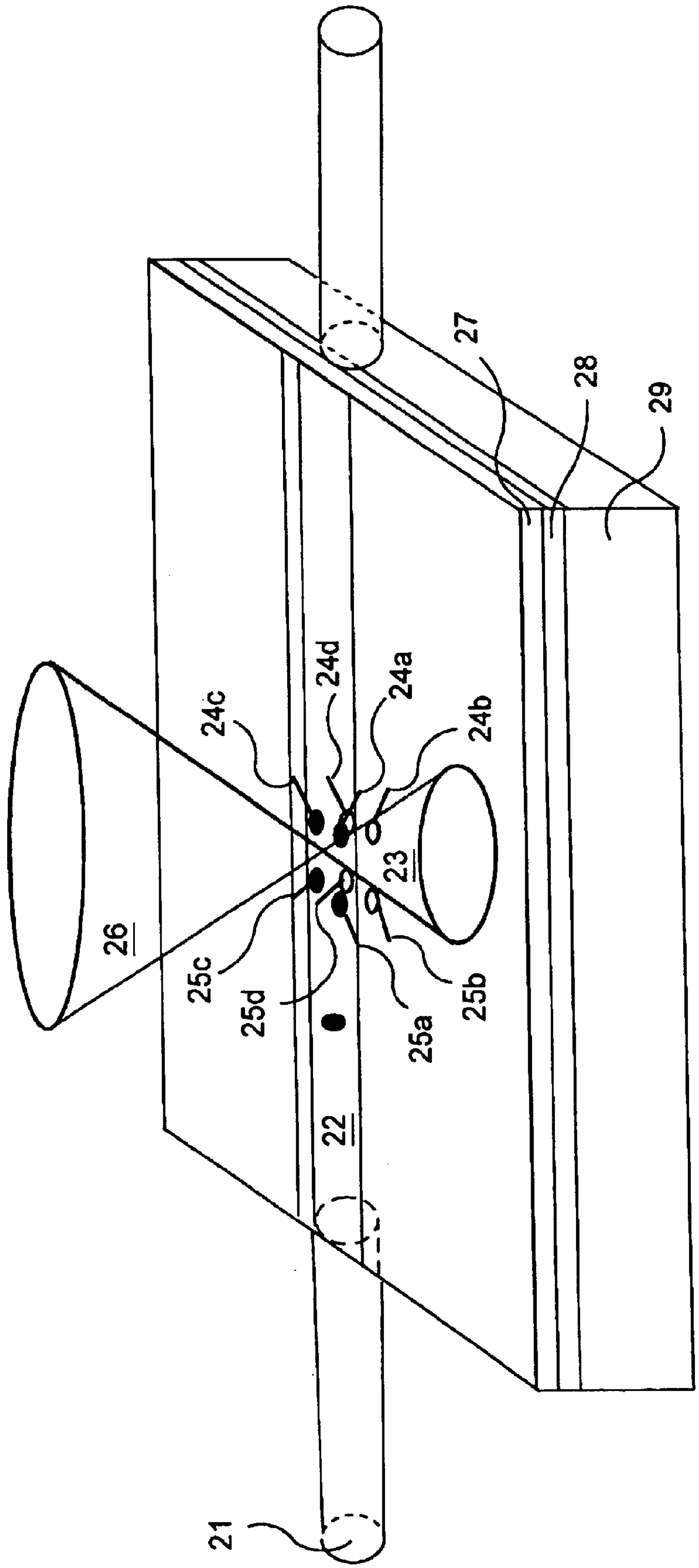
FIG. 2: another schematic representation of the arrangement of the field cage electrodes and an optical cage.

FIG. 2 shows an expanded diagram of a system to measure the optically-induced forces that act on a particle trapped in the focus. The microfield cage is formed by microelectrodes that are on facing surfaces of the substrate 27, 29. The substrates 27, 29 are separated by a spacer 28 that forms a suspension gap in which the investigated particle is exposed to the field of the microfield cage. The top substrate in FIG. 2 is sufficiently thin for the focus of the optical cage to be adjustable in the suspension area.

Through an opening 21, cells or other microparticles suspended in a solution are injected into the channel 22 and then reach the field cage 23 whose output electrodes 24*a*–*d* are subjected to a high-frequency field (kHz or MHz with any signal shape such as square, sinusoidal, triangular or any other signal shape, and with an amplitude of a few mV to some 10 V). By first applying electrical potential to the microelectrodes on one side, only an electrical field barrier for inserted microparticles is formed in the channel 22. If a particle is in the cage 23, the input electrodes 25*a*–*d* are also switched on and/or the flow is stopped. The particle is moved in the field cage area with the laser beam 26 as described above, and the optically-induced forces are measured. The phase shift typical for the electrode signals for electrical trapping to control two possible types of alternating fields and two rotation fields (2* AC field or 2*rot field) are summarized in Table

TABLE 1

Phase controls of the electrode signals of an octopole

| Field type | El. 25b | El. 24b | El. 24d | El. 25d | El. 25a | El. 24b | El. 24c | El. 25c |
|---|---|---|---|---|---|---|---|---|
| AC field | 0° | 180° | 0° | 180° | 0° | 180° | 0° | 180° |
| AC field | 0° | 180° | 0° | 180° | 180° | 0° | 180° | 0° |
| Rot field | 0° | 90° | 180° | 270° | 180° | 270° | 0° | 90° |
| Rot field | 0° | 90° | 180° | 270° | 90° | 180° | 270° | 0° |

In contrast to the AC field, torque is exerted on the particle in the rot field that causes the particle to rotate (last line of the table 1) which can also be used to determine force. The torque is compensated with the values of the next-to-last line of table 1.

In the present example, flat electrodes have been created on two glass substrates 27, 29 using methods known from semiconductor technology that are mounted liquid-tight from above by a spacer 28 so that they are immersed in the channel liquid 22. For the laser to be highly focussed, one of the glass substrates (27 in this instance) must be very thin. In the present example, substrate 27 is 150 to 200 micrometers thick, and substrate 29 consists of 0.5 to 1 mm-thick glass or plastic.

Figure 3:
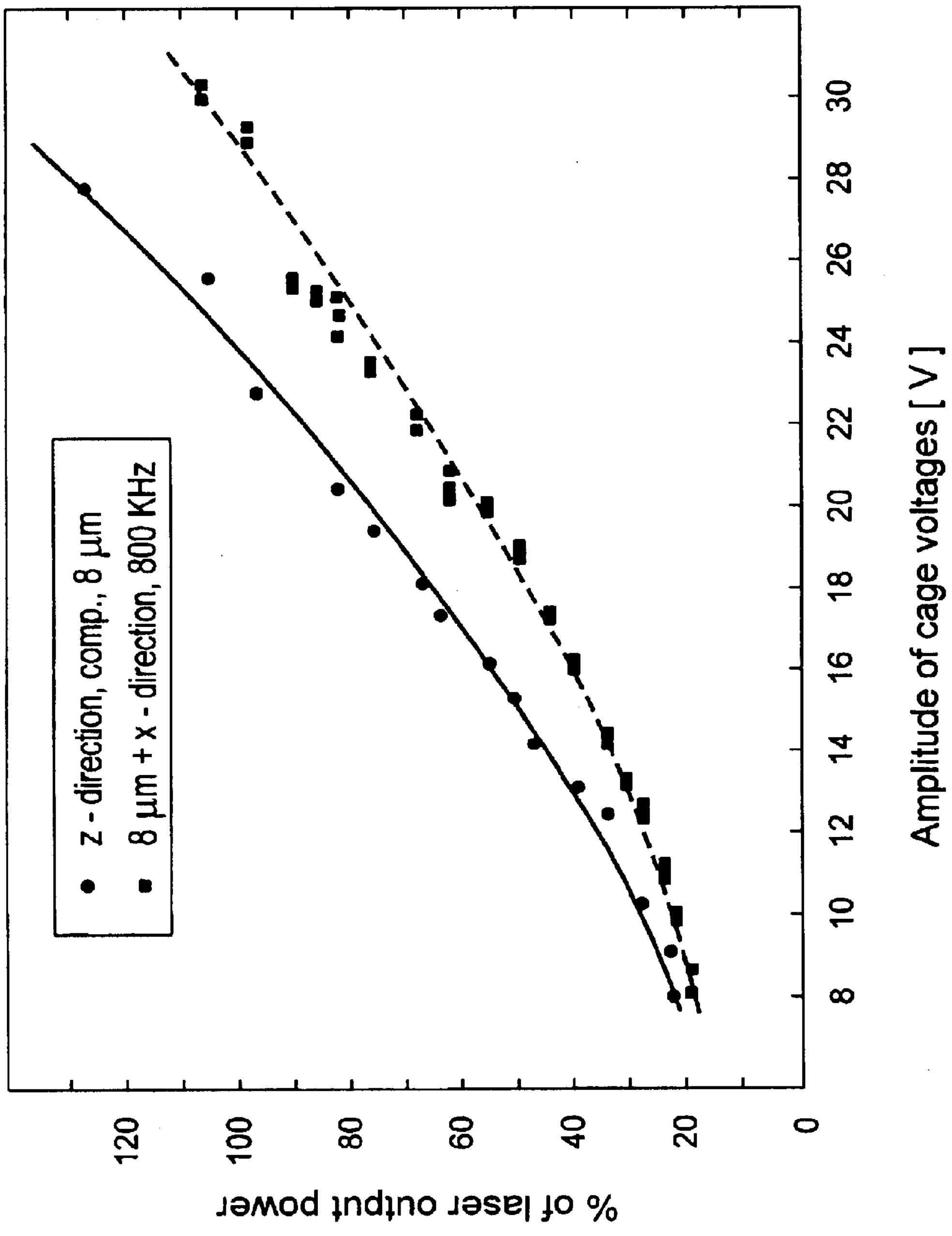
FIG. 3: a curve to illustrate experimental results.

As the laser output increases, so do the optically-induced forces so that correspondingly rising electrical field strengths, i.e., signal amplitudes, are necessary to bring about the cited transition between the minimum field levels. This is shown in FIG. 3 with reference to the experimental results. This curve shows the relationship between the laser output, i.e. the level of optically-induced force, and the amplitudes of the cage voltages, i.e. the amplitudes of the electrical potentials that are applied to the microelectrodes. As the laser output in-creases, greater amplitudes of the cage voltage are necessary to cause the particle to move between the focus and the capture point. It can clearly be seen that the capturing power of the optical trap is weaker in the z direction (top curve) than in the z or y direction (bottom curve).

Figure 4:
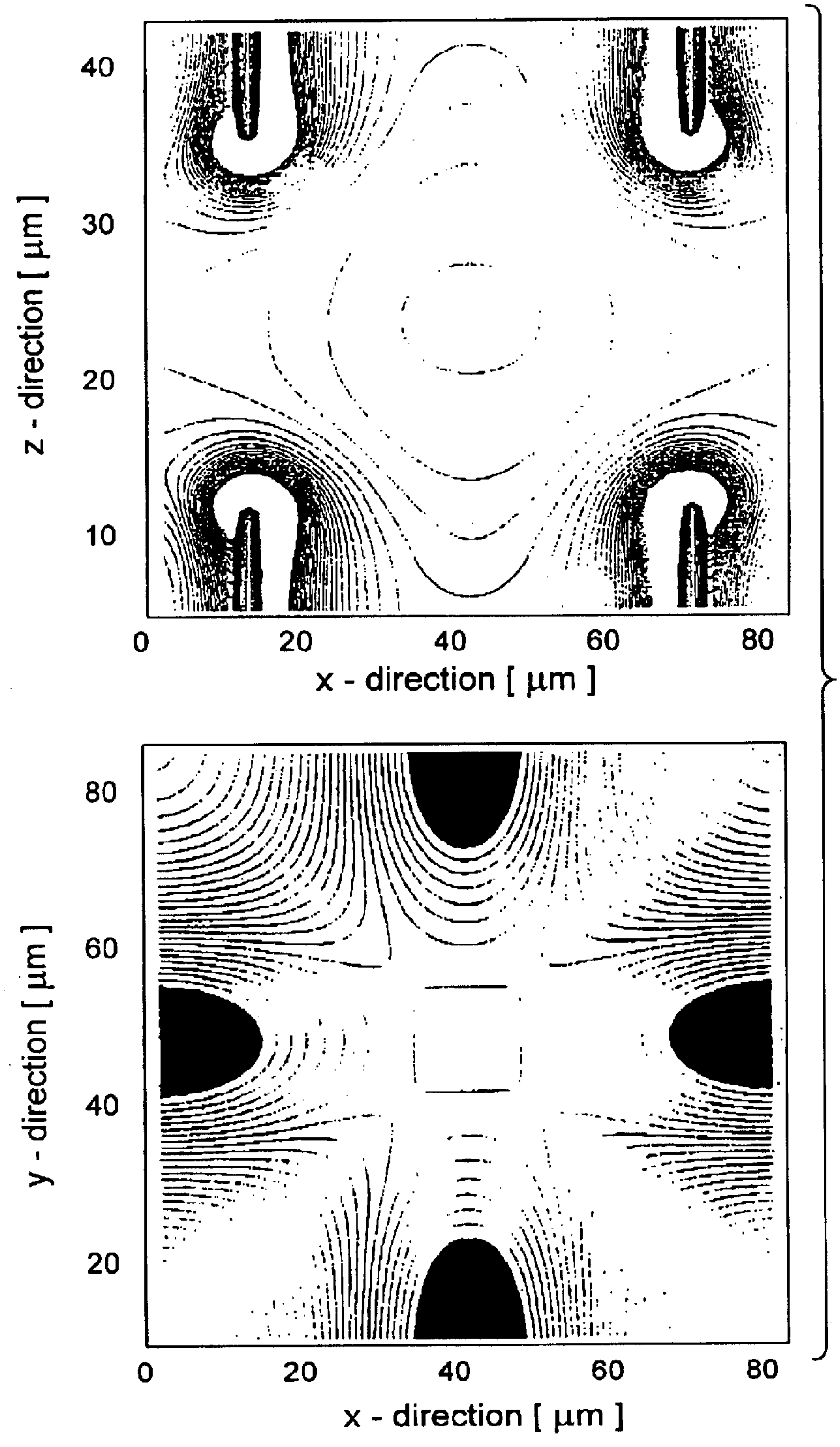
FIG. 4: an example of the field distributions of an octopole field cage.
Figure 5:
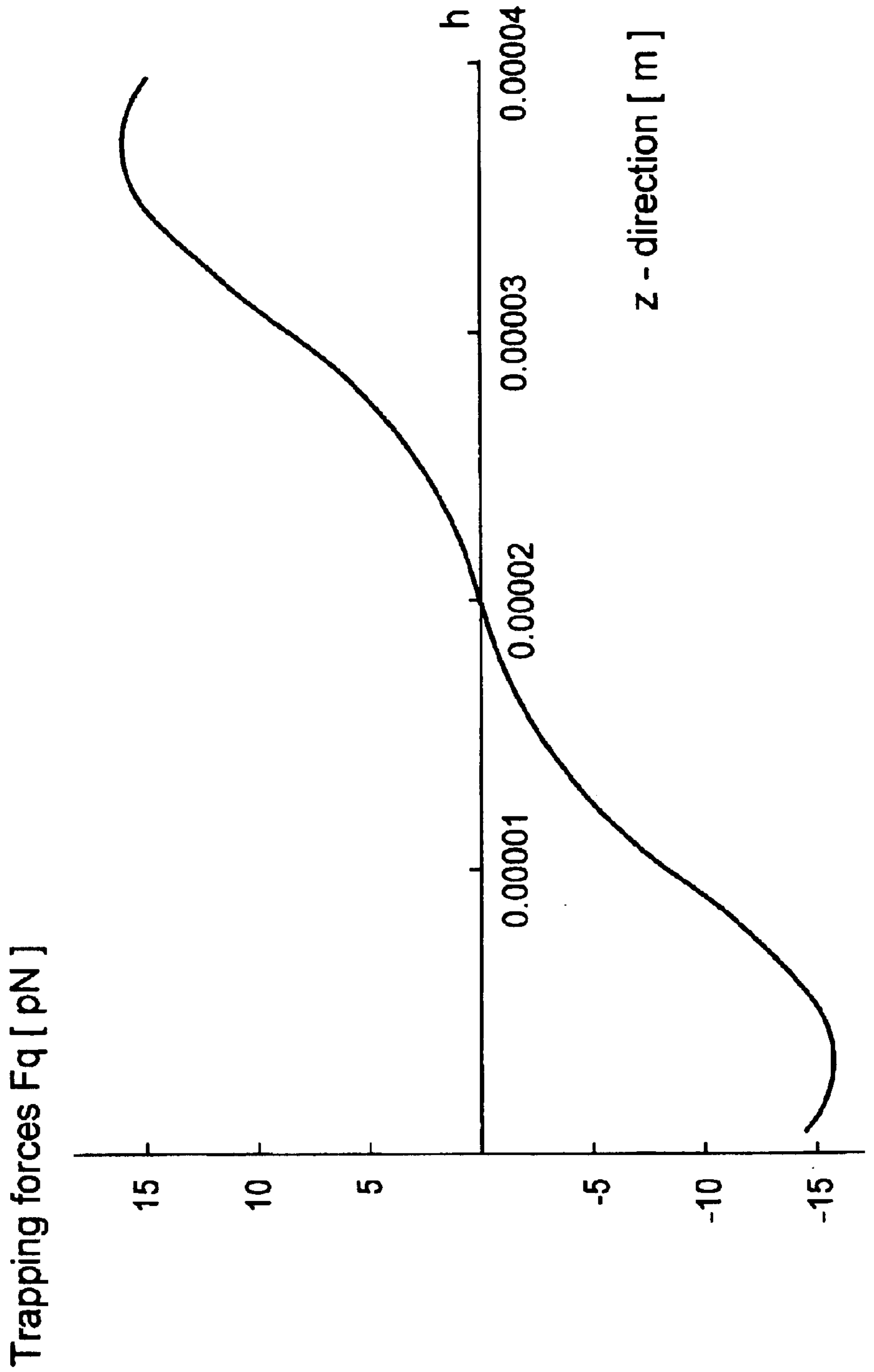
FIG. 5: a curve to illustrate the capture force of the field cage in the z direction shown in FIG. 4.

The capture forces of the laser tweezers in the z direction shown in FIG. 5 result from the field distribution in FIG. 4 (obtained from a single numerical calculation taking into account the actual electrode dimensions in FIG. 1 and distances) and the passive electrical properties of the test particle (in this case, a latex bead with a diameter of eight micrometers). The curve shown refers to a signal amplitude of the cage electrodes of 10 V. Experimentally, amplitudes of up to 30 V were applied. Given a quadratic dependency on the capture force of the electrical cage, this corresponds to a maximum detectable force of approximately 150 pN with a resolution in the pN range and below. These measuring results correspond well with the theory of laser tweezers (see A. Ashkin in *Biophys*. J., Vol. 61, 1992, p. 569). Electrodes with a finer design allow much higher signal amplitudes and hence much higher electrically-induced forces to be generated so that substantially greater force can be detected.

A particular advantage of the invention is that the method is quick and easy to carry out, especially in the environmental medium that will be later utilized using comparable conditions with the same particles for later investigation or manipulation. In addition, this procedure is not limited to specific particles and surface shapes; particles with any shape can be used. The force exerted on the adhering particle groups (such as aggregates, etc.) of any shape can also be measured.

Examples of measuring the force acting on adhering particle groups and exerting force on particles to manipulate particle groups will be described in the following with reference to FIGS. 6–8.

Figure 6:
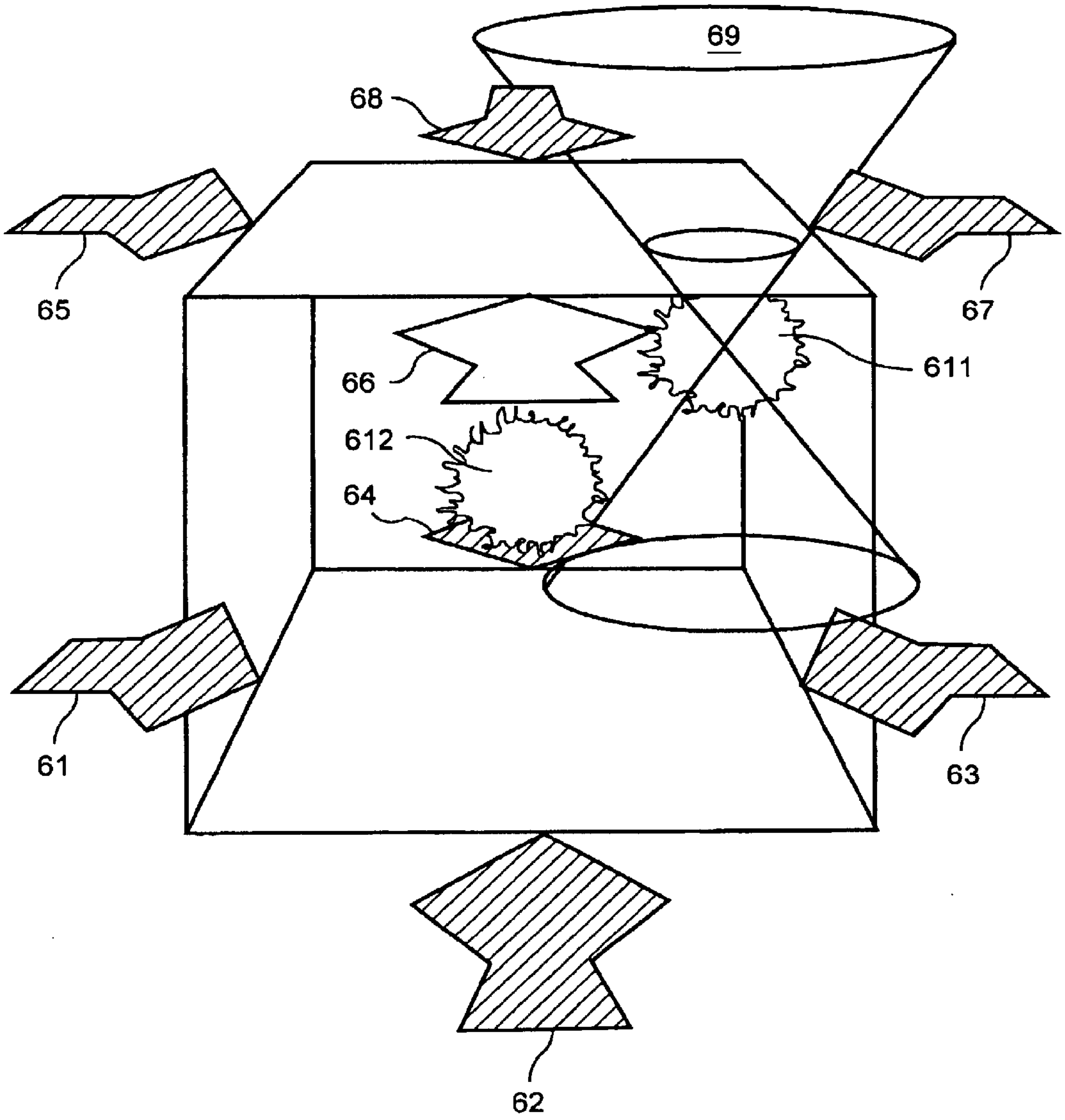
FIG. 6: a diagram of the arrangement of cells in an optical cage and a capture area according to a second embodiment of the invention.

FIG. 6 shows a microelectrode arrangement in an octopole shape with microelectrodes 61–68 analogous to FIG. 1. The microelectrodes 61–64 and 65–68 are in a microsystem set up for a process according to the invention in two spaced levels to form an electrical field cage with a minimum field level that forms the capture area or point. The electrical field cage is in the microelectrode arrangement that is sketched by the cube in FIG. 6. Reference number 69 refers to a light beam (preferably laser beam) focussed in the microelectrode arrangement. A first particle as a biological cell 611 is in the focus of the light beam 69. A second particle that is also a biological cell 612 in the illustrated example is in the capture point of the electrical field cage. The bond force between the particles can be determined as discussed below analogous to measuring the optically-induced force by observing the transitional movement of a particle from the focus to the capture area as discussed above.

First two cells 611, 612 are sequentially introduced into the microelectrode arrangement 61–81. This is preferably done with the injection process explained with reference to FIG. 2 where the microelectrode arrangement is connected to a channel structure of a fluid microsystem. The first cell 611 is injected into the microelectrode arrangement and held in the electrical capture area (trap area) after the octopole field is completely under control. Then the first cell 611 is taken by the optical cage formed by the laser beam 69 and positioned at a distance from the capture area. Then the second cell 612 is injected and positioned in the trap area, e.g. in the middle of the microelectrode arrangement 61–68. However, any other technique can be used to introduce the microscopic particles into the microelectrode arrangement. Depending on the use, both particles can be like or different biological cells or biological cells, cell components, and/or synthetic particles with specific active ingredients.

Subsequently, the cells 611, 612 contact each other, and an adhesive bond is formed between both cells. The adhesive bond can e.g. arise from one of the following techniques. First off, it is possible to release the first cell 611 by shutting off the laser beam 69 and then move it under the effect of the electrical field to the capture area of the electrical field cage where it contacts the second cell 612, and the adhesive bond is formed. It is also possible to adjust the focus of the laser beam 69 in reference to the capture area so that the first cell 611 contacts the second cell 612 or is even pressed against it with a predetermined force. The mutual forces of the cells pressed against each other can be derived from the electrical field strength in the capture area and the optical force in the focus of the laser beam 69 e.g. determined by the above-cited technique. To quantitatively compare the measured bonding force, the adhesive bond is set for a predetermined period (e.g. approx. 0.1–10 sec.). Longer times up to e.g. 1,000 seconds are also possible.

After the contact period that is set depending on the application, the binding forces (interactive forces, adhesion strength) between the cells can be determined as follows. The force is measured analogously to the above-cited measurement of the optically-induced force acting on individual particles by varying the field properties and determining the field strengths in the electrical capture area and optical cage at which the cells tear away from each other. For example, at a given electrical potential amplitude, the laser beam 69 focussed on the first cell 611 is moved repeatedly so that the focus moves away from the capture area. If the first cell 611 does not move with the focus, the focus is reset and the cell is subjected to stepped-up light power. When the optical force induced by the light power is known, the force it takes to tear two cells apart and hence the mutual binding force can be calculated from the light power it takes to entrain the first cell 611 by moving the focus. Other possibilities for measuring this force are to vary stepwise the electrical potential amplitudes and move the location of the capture area by correspondingly controlling the microelectrodes 61–68. Combinations of both techniques can be used to vary the field properties.

A particular advantage of this procedure is that it can be repeated with a given pair of particles, and any desired cell contact time can be precisely set.

Preferred applications for the procedure described with reference to FIG. 6 (that until now was unacceptably expensive) are to contact two or more like or different biological cells for a precise period. The process is therefore useful for pharmacological and medical diagnostic tests. An example of a process in this context is to stimulate the second cell 612 by temporarily contacting it with the first cell 611 to change the binding behavior of the second cell 612. The changed binding behavior can then be tested by coupling a third cell (not shown). Another example is to screen peptide or other molecular libraries by introducing a first type of cell into the microelectrode arrangement. The surface receptors of the first cell are then contacted with a test or active substance from a molecular library through the suspension solution in the microsystem. Then a second cell (or a synthetic particle with surface molecules that bond well) is brought to the first cell. The above-explained measurement of the bonding force can yield one of the following results. If the bonding sites of the first cell are already saturated with the active substance, there is no (or only a weak) binding to the test cell. Otherwise, a strong bond is formed with the test cell. Biological cells can be accordingly evaluated and sorted in reference to their reaction of specific active substances.

Another example of stimulating biological cells will be explained below with reference to FIG. 7. FIG. 7, like FIGS. 1 and 6, shows a microelectrode arrangement with microelectrodes 71–78 and a light beam 79 focussed in the micro-electrode arrangement.

Like the above-explained injection or flow principle, a first cell 711 is captured in the electrical capture area of the microelectrode arrangement 71–78 and positioned. A second cell 712 or a synthetic particle with an active ingredient is captured with the light beam 79 and moved along a set path 713 past the first cell 711, or it contacts the first cell for a predetermined time. Even when the cells or particles do not bond or adhere, a chemical signal can be transmitted when the surfaces contact each other that can result in a subsequently analyzable change in one or both cells. Instead of the individual cells, cell groups or aggregates can be joined and separated to mutually stimulate each other for a set period under the effect of predetermined forces.

This procedure to stimulate biological cells or cell groups has numerous applications in medicine and biotechnology.

Stimulation e.g. by applying a medication from the environmental solution that up to now could only be done with a great deal of effort can now be carried out for specific cells under defined and reproducible conditions. In living organisms, such stimulations (or inhibitions) usually occur from interactions between cells that are closely adjacent or must contact each other. The conditions that arise in organisms can hence be advantageously simulated with the process according to the invention.

Figure 7:
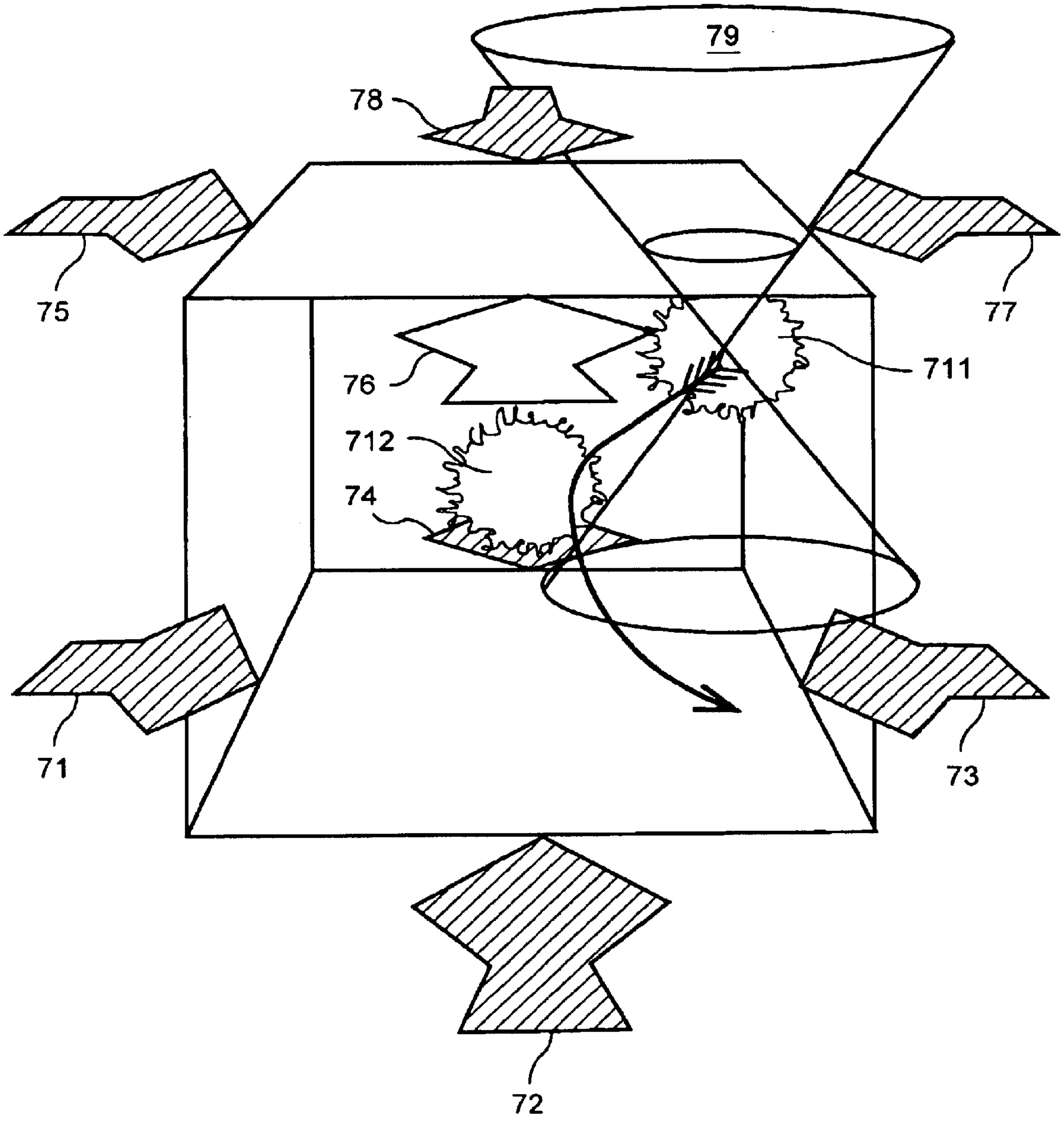
FIG. 7: a diagram of the arrangement of cells in a microelectrode arrangement according to a third embodiment of the invention.

The procedure illustrated by FIG. 7 can advantageously be with or without the above-cited measurement of optically-induced forces by setting predetermined field properties. The same holds true for the process explained with reference to FIG. 8 for exerting set forces on cells or cell groups to form aggregates.

Figure 8:
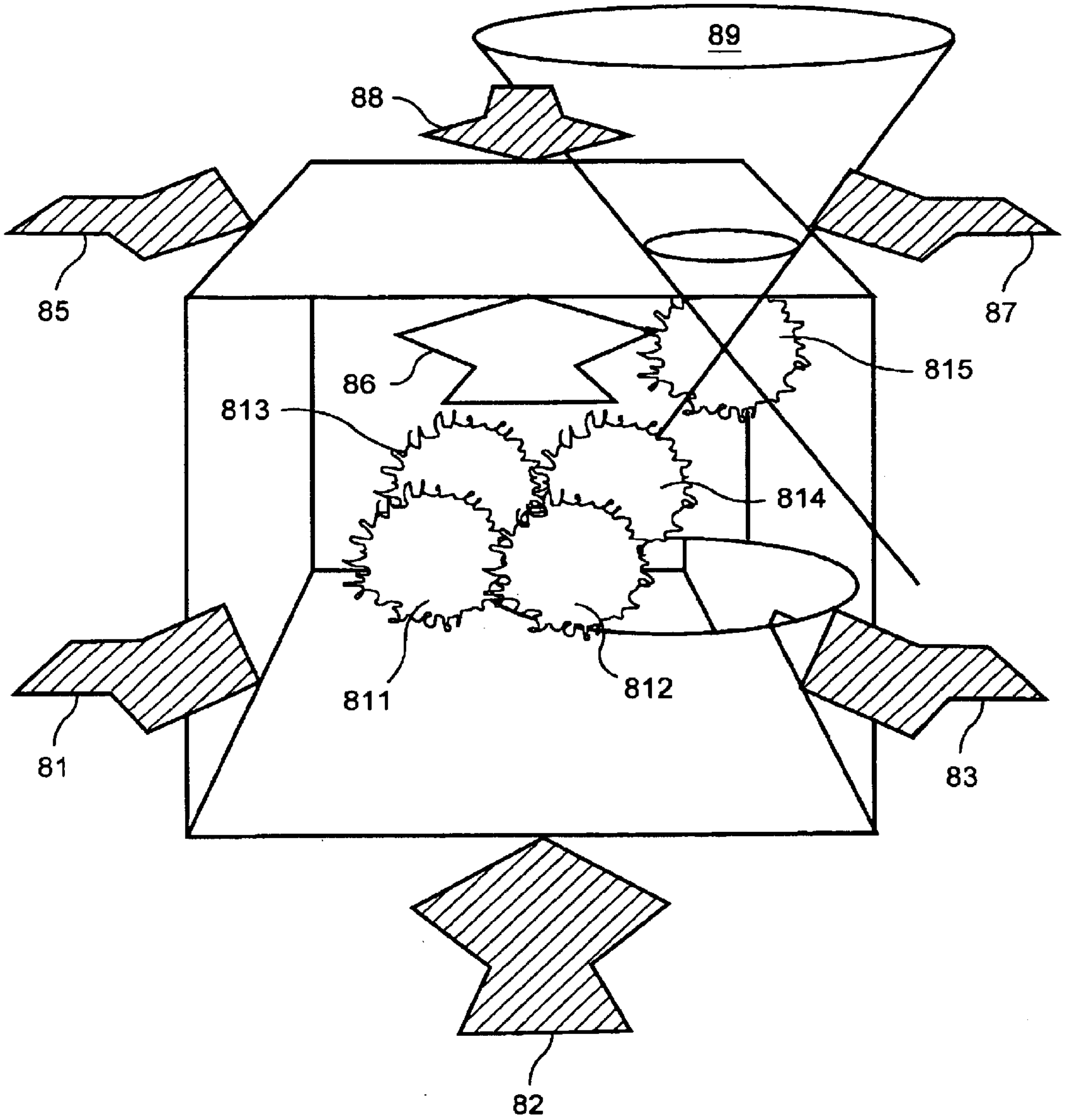
FIG. 8: a diagram of the arrangement of cells in a microelectrode arrangement according to a fourth embodiment of the invention.

FIG. 8 shows a microelectrode arrangement with microelectrodes 81–88 and a light beam 89 in the microelectrode arrangement.

According to the above-discussed injection or flow technique, numerous biological cells are injected into the interior of the microelectrode arrangement. With the optical cage of the light beam 89, cells are specifically moved into the capture area and positioned there, possibly relative to existing cells. For example, four cells 811–814 are in the electrical capture area in FIG. 8 to which a fifth cell 815 is added at a set position (corresponding to the arrow). The fifth cell 815 is pressed for a set period with a set force against the formed cell group 811–814 to allow the formation of bonding forces in this predetermined relative position.

Any cell aggregate with a predetermined shape can be constructed in this manner. This procedure can also be implemented using negatively polarized synthetic microparticles that can be repulsed by the microelectrodes in the electrical capture area (negative dielectrophoresis).

Figure 9:
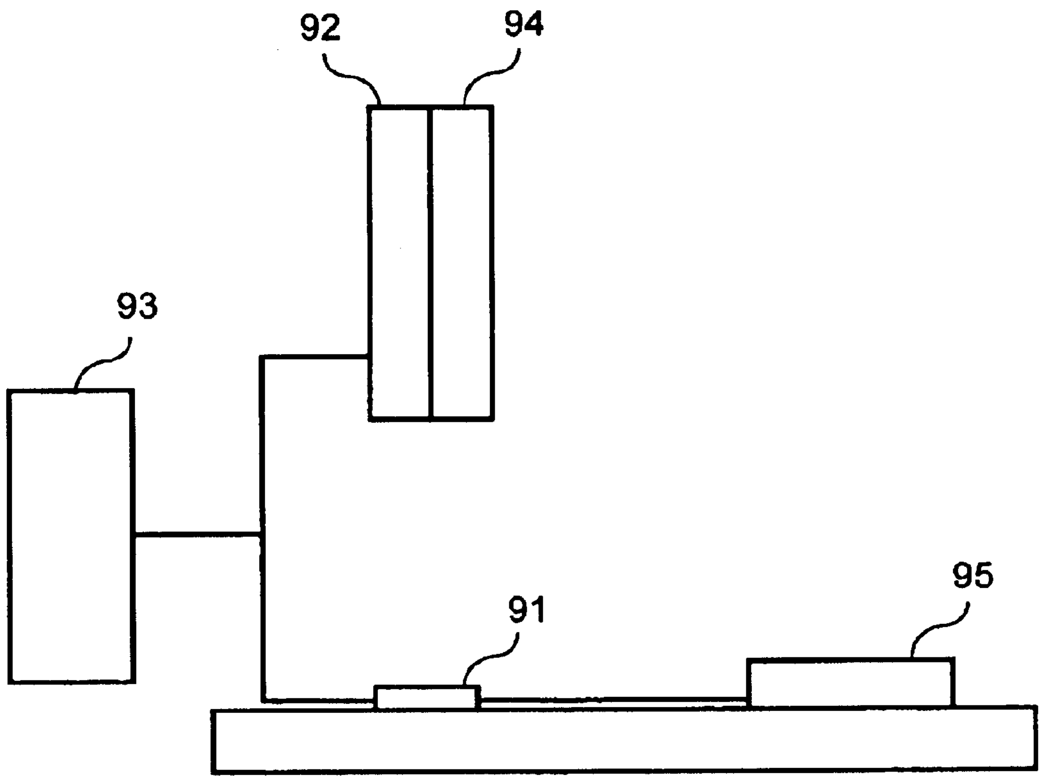
FIG. 9: a schematic representation of a device according to the invention.

A device according to the invention consists of an arrangement of a fluid microsystem 91, an illumination device 92 to generate an optical cage in a microelectrode arrangement of the microsystem 91, where the microsystem 91 and the illumination device 92 are adjustable relative to each other with an adjusting device 93, and a monitoring device and/or sensor 94 (such as a microscope) as schematically portrayed in FIG. 9. The microsystem is provided with a fluid and potential control 95 as known as such. The illumination device 92 is e.g. a prior-art pair of laser tweezers as known as such that can contain a diode laser or a semiconductor laser as the light source and has a microscope arrangement for focussing.

What is claimed is:

1. A procedure to exert or measure optically-induced forces which are capable of moving at least one particle or holding at least one particle in a focus of an optical cage formed with a light beam, comprising:

a) positioning the focus in a microelectrode arrangement in which an electrical field is formed that has a field gradient which forms a three-dimensional electrical capture area, said electrical capture area representing an electrical field cage with a capture point at a minimum electrical field level of the capture area, wherein the focus is positioned at a distance from the capture point b) positioning said at least one particle at one of the focus and the capture point, c) varying at least one parameter selected from an amplitude of said electrical field, a light power of said light beam and the distance of the capture point from the focus until the particle moves between the focus and the capture area, and d) exerting said optically-induced forces, wherein said at least one particle is at least temporarily moved between the focus and the capture area, or measuring said optically-induced forces, wherein said at least one parameter varied in step c) is detected when said at least one particle moves between the focus and the capture point.

2. The process according to claim 1 in which a particle is placed in the focus or capture area to measure optically-induced forces, and the optically-induced forces are measured from the amplitude of the electrical field and the distance of the capture area from the focus when the particle moves from the focus to the capture area or vice versa.

3. The process according to claim 2 in which the optically-induced forces are repeatedly measured for all relevant directions in space corresponding to mutual alignment of said positions of said focus and said capture area.

4. The process according to claim 2 in which the optical cage is calibrated by determining a relationship between the light power to generate the optical cage and the forces induced on a particle in the optical cage.

5. The process according to claim 1 in which the distance between the focus and capture area is at least one-tenth of a particle diameter.

6. The process according to claim 1 in which the capture area is a capture point that is in a beam field of the optical cage so that the at least one particle moves back and forth between the capture point and focus when the amplitude of one of the electrode signals and light power is varied, and an associated value of the amplitude is used to measure the optically-induced forces.

7. The process according to claim 1 in which numerous particles are sequentially injected with said optical cage into said capture area, wherein said particles are positioned in predetermined positions within the capture area relative to other particles in the capture area.

8. The process according to claim 1 in which the light beam of the optical cage is adjusted and one of a capture quality and symmetry of the optical cage are measured.

9. The process according to claim 1, in which passive electric properties of said at least one particle are characterized based on the measured optically-induced forces.

10. The process according to claim 1 in which an electrode of the microelectrode arrangement is alternatively supplied with at least one of signals phase-shifted 180° and rotation-generating signals with a predetermined phase division.

11. The process according to claim 1 in which at least one field barrier is formed between said capture point and said optical cage.

12. The process according to claim 1 in which a particle movement is detected by one of optical and electrical detection.

13. The process according to claim 1 in which the particles are synthetic or natural particles with a size less than 200 μm.

14. The process according to claim 1 in which the particles are biological cells or their components.

15. The process according to claim 1 in which the movement of the particle between the capture area and the focus is used to adjust the optical cage.

16. Calibrating a laser tweezer by exerting optically-induced forces on at least one particle and measuring said forces with a procedure according to claim 1.

* * * * *